United States Patent
Rogers et al.

(10) Patent No.: US 6,974,425 B2
(45) Date of Patent: Dec. 13, 2005

(54) APPARATUS AND METHOD FOR IMPLEMENTING HYDRO-ACOUSTIC THERAPY FOR THE LUNGS

(75) Inventors: Peter H. Rogers, Atlanta, GA (US); Gary W. Caille, Roswell, GA (US); Alice L. Rogers, Atlanta, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 522 days.

(21) Appl. No.: 09/842,610

(22) Filed: Apr. 26, 2001

(65) Prior Publication Data

US 2002/0014235 A1 Feb. 7, 2002

Related U.S. Application Data

(60) Provisional application No. 60/200,484, filed on Apr. 28, 2000.

(51) Int. Cl.[7] .................................................. A61H 1/00
(52) U.S. Cl. ................................................ 601/46; 601/47
(58) Field of Search ......................... 601/46–49, 55, 601/68, 69, 84, 86, 154–158

(56) References Cited

U.S. PATENT DOCUMENTS

| | | | |
|---|---|---|---|
| 4,216,766 A | 8/1980 | Duykers et al. | 128/773 |
| 5,695,455 A | 12/1997 | Alton, Jr. et al. | 601/47 |
| 6,027,464 A | 2/2000 | Dahlquist | 601/148 |
| 6,190,337 B1 | 2/2001 | Nedwell | 601/46 |

*Primary Examiner*—Michael Brown
(74) *Attorney, Agent, or Firm*—Thomas, Kayden, Horstemeyer & Risley, L.L.P.

(57) ABSTRACT

The present invention involves an apparatus for implementing hydro-acoustic therapy for the lungs on a patient and a method for the hydro-acoustic therapy (HAT) for the lungs. The HAT apparatus includes a chamber filled with a fluid, particularly water. The HAT apparatus also has an acoustic generator for generating low frequency acoustic waves in the fluid. A patient is positioned in the chamber and partially submersed in the fluid for treatment. In another aspect, a method for implementing hydro-acoustic therapy for the lungs includes the step of placing a person in the apparatus described above such that a body of the person is immersed in said occurs. Then, introducing acoustic vibrations into the fluid. The vibrations, if properly tuned, cause the mobilization of respiratory secretions in the person.

25 Claims, 4 Drawing Sheets

APPARATUS AND METHOD FOR IMPLEMENTING HYDRO-ACOUSTIC THERAPY FOR THE LUNGS

CROSS-REFERENCE TO RELATED APPLICATION

This application claims priority to copending U.S. provisional application entitled, "Hydroacoustic Lung Therapy," having Ser. No. 60/200,484, filed Apr. 28, 2000, which is entirely incorporated herein by reference.

TECHNICAL FIELD

The present invention relates generally to therapeutic treatments for medical patients, and, more particularly, to a method and apparatus for causing the mobilization of respiratory secretions through hydro-acoustic lung therapy.

BACKGROUND OF THE INVENTION

Cystic Fibroses (CF) is a recessive genetic disease caused by mutations in a membrane-associated protein, which promotes transcellular movement of chloride ions in airway epithelia and other tissues. In the lungs, defective function of the membrane-associated protein results in abnormally thick secretions in the lower airways which plug small bronchioles and provide an environment for chronic endobronchincal bacterial infection. Despite recruitment of vast numbers of neutrophils, bacterial clearance is ineffective, and the airways of the lungs are damaged by free radical species and prostheses released by the neutrophils. In addition, as the recruited neutrophils decompose in the airway, the DNA from their nuclei markedly increase the viscosity of the lower airway secretions, leading to further airway blockage and infection. The end result of this above-identified cycle is destruction of bronchial airway structure and progressive loss of lung function in the CF patient. Despite significant improvements in clinical management, respiratory failure and related pulmonary complications account for over ninety percent of CF mortality.

Since pulmonary disease is the primary cause of morbidity and mortality in CF, considerable effort has been directed to increase the mobilization of the abnormally thick airway secretions through various forms of chest physiotherapy. In the normal respiratory system, there are three primary mucus transport mechanisms. First, as is predominate in the smaller airways of the lungs, is a conveyor-like effect of a coordinated beating of airway epthocilia. In the larger airways, the second method of mucus transport is the high velocity airflow associated with coughing. Coughing tends to sheer mucus off airway surfaces and propels it towards the pharynx. The third mechanism of transporting mucus through the lungs is termed cephalad airflow bias of tidal breathing. Cephalad airflow bias results from greater expiratory versus inspiratory airflow due to compression of the intrathoracic airways during expiration. However, the abnormal composition and increased amount of tracheal bronchial secretions in the airways of a CF patient impede all of these natural mechanisms of mucus clearance.

For this reason, several forms of chest physiotherapy have been developed. These methods of chest physiotherapy are intended to assist in pulmonary mucus clearance and are presently widely used for CF patients. The mechanism underlying all modes of chest physiotherapy currently in use is vibration of the airway surfaces, either through external chest compression or by oscillatory airflow, to promote increased cephalad-induced and/or cough-induced mobilization of airway secretions.

Currently, the most common form of chest physiotherapy is manual chest physiotherapy. In manual chest physiotherapy a trained caregiver strikes the patient's chest with cupped hands. This striking motion is usually complimented with postural drainage, a systematic form of directing mucus from the peripheral to the central airways through a series of gravity-assisted patient positions and therapist simulation. Each physiotherapy session is coupled with a period of huffing and coughing to remove sputum. While this method of therapy is somewhat effective, manual chest physiotherapy is labor intensive because it must be performed by a therapist or trained caregiver. The efficacy of manual chest therapy depends on the skill and diligence of the therapist. For this reason, manual chest physiotherapy may be expensive and/or time consuming for the therapist and patient. Additionally, the striking of the chest may cause discomfort to the patient or damage to a more fragile patient's ribcage.

Various mechanical devices have been developed in an effort to standardize and increase the efficiency of chest physiotherapy. Among the most widely employed forms of mechanical chest physiotherapy are various hand-held compressors which deliver external chest vibration, high frequency chest compression administered through an inflatable jacket, and devices such as a FLUTTER™ device which delivers internal airway stimulation from pulsating airflow via the mouth.

The high frequency chest compression (HFCC) method of chest physiotherapy is very commonly employed today. HFCC is administered via a product called the VEST™. In clinical studies with CF patients, use of the VEST™ has been shown to be a practical, automated method of chest physiotherapy, and is an improvement over manual therapy to the extent that it allows for increased patient independence. HFCC, via oscillating chest compression, stimulates cough with its associated mucus shearing airflow spikes, and the compression of the thorax during expiration results in increased expiratory airflow. It is hypothesized also that HFCC at certain frequencies promotes a longer ciliary brush stroke, thereby enhancing mucus transport.

The VEST™ device consists of an inflatable vest structure which is strapped onto the patient's torso. The inflatable vest structure is attached by supply tubes to an air compressor. The air compressor is powered such that it can force air into the vest worn by the patient at set frequencies and amplitudes. In this way, the vest that the patient wears is inflated to compress the patient's chest at set frequencies and amplitudes.

With the present mechanical devices such as the VEST™, the oscillating pressure administered to the chest wall is not transmitted equally across the chest to the underlying lung. Increased mucus transport only occurs in those portions of the lungs directly covered by the isolating pressure vest. In particular, with the VEST™ device the lungs are excited from the sides but not from the top or bottom. The pressure administered by the VEST™ device is not uniform. The pressures applied to the patient's chest varies greatly. Additionally, the frequency at which the vest operates is not fine-tuned such as to optimize airway stimulation with the least amount of applied external energy. Generally, in clinical use of the VEST™, patients adjust the frequency and amplitude of the applied chest wall stimulation to what they believe provides the best results or to the maximum they can tolerate.

In addition to the above-referenced shortcomings of the prior art chest physiotherapy regimens, the current methods of chest physiotherapy are generally quite uncomfortable.

Most of the current methods of chest physiotherapy require a force to be exerted on the external chest cavity of the patient. This is disadvantageous to all patients, but particularly to those who are more prone to rib or chest injury due to the impact, such as frail or elderly patients and very young patients.

Therefore, it would be desirable to have a method and apparatus for chest physiotherapy that does not involve a trained caregiver or physiotherapist, such as to minimize cost, increase the patient's independence, and also involves a marginal, if any amount of impact to the CF patient's chest. It is also desirable to have a method and apparatus for chest physiotherapy that does not cause discomfort to the patient, applies more uniform stimulation to the lungs and excites the entire lung. The invention described in detail below meets the limitations of the prior art.

SUMMARY OF THE INVENTION

Briefly described, the present invention comprises an apparatus for affecting hydro-acoustic therapy for the lungs on a patient and a method of implementing the hydro-acoustic therapy (HAT) for the lungs. HAT, for purposes of this disclosure, encompasses treatment using acoustic vibrations, or sound, in a liquid environment. An embodiment of a HAT apparatus comprises a chamber filled with a fluid, particularly water. The HAT apparatus also has an acoustic generator for generating low frequency acoustic waves in the fluid. A patient is positioned in the chamber and partially immersed in the fluid for treatment. Specifically, a patient submerged in a fluid, such as water, to a neck of the patient.

In another aspect, a method for implementing hydro-acoustic therapy for the lungs includes the step of placing a person in the apparatus described above such that a body of the person is immersed in said fluid. Then, introducing acoustic vibrations into the fluid occurs. The vibrations, if properly tuned, cause the mobilization of respiratory secretions in the person.

The HAT method and apparatus described herein can result in effective treatment of many debilitating ailments. For example, HAT may prove to be a particularly effective treatment for cystic fibrosis patients, chronic obstructive lung disease, pneumonia, and lung cancer, by way of example.

HAT is also an improvement over the prior art for several reasons. HAT can be operated such that a lung of the patient moves uniformly for more effective treatment. HAT does not require physical impact with a chest of the patient, such as required by HFCC. Additionally, HAT does not require the presence of a trained caregiver or physical therapist. Finally, it is common to administer drugs to patients, such as cystic fibrosis patients, through airborne inhalants. It is believed that the absorption of air-delivered drugs, if administered during HAT, will increase due to the operation of HAT.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENT

Figure 1:
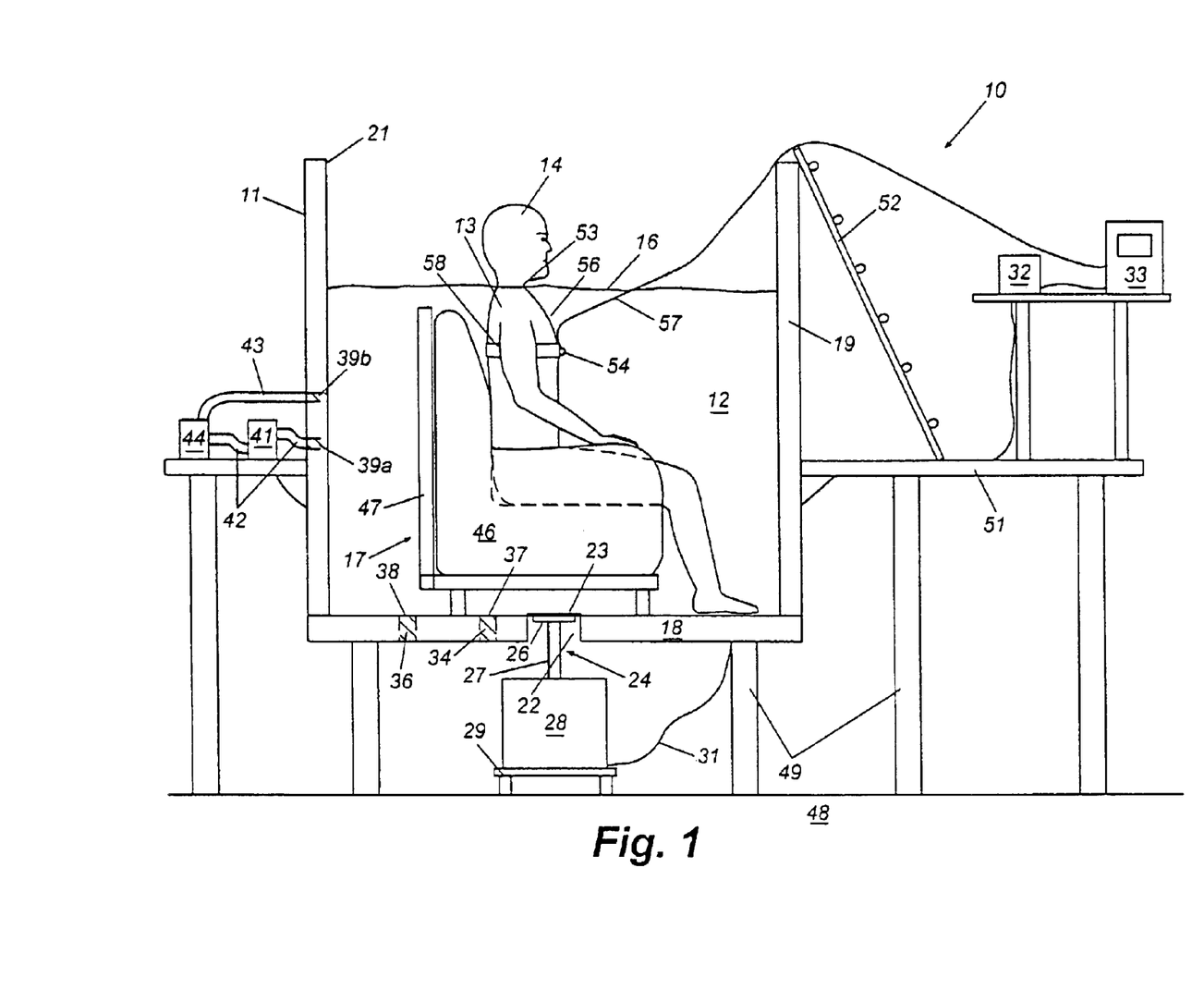
FIG. 1 is a cut-away side view of an exemplary hydro-acoustic therapy for the lungs apparatus according to the present invention.

FIG. 1 is a cut-away side view of an exemplary hydro-acoustic lung therapy ("HAT") apparatus 10. The exemplary HAT apparatus 10 includes a chamber 111 for holding a fluid 12. As depicted in FIG. 1, the exemplary apparatus 10 has the fluid in the chamber 11, but the chamber 11 is not fully filled with the fluid 12. A person, or patient 13 is positioned in the fluid 12 such that a head region 14 of the patient 13 protrudes above the surface 16 of the fluid 12. Preferably, the HAT apparatus 10 is designed such that the person 13 will sit on a supporting structure 17 in the fluid 12.

I. Construction of the Preferred Embodiment

The chamber 11 preferably comprises a cylindrically shaped cavity manufactured from a structurally rigid, or stiff material. The chamber 111 has a circular bottom wall 18 and a single, cylindrically shaped sidewall 19 attached to a periphery of the bottom wall 18. The top portion 21 of the chamber 11 is open. The particular shape of the chamber 11 is not required to be cylindrical; however, a cylindrically shaped chamber 11 is preferable because the cylindrical shape insures uniform sound reflection and eliminates edge reflections of acoustical waves. The chamber 11 could be shaped as a cube or spherical, for example. These features are generally beneficial to the HAT method described below. Further, the chamber 11 of the preferred embodiment 10 is large enough so that the patient 13 can easily fit in the chamber 11, as depicted in FIG. 1. The exemplary HAT apparatus 10 has a chamber that is 1.2 meters diameter and 1.5 meters tall. The cylindrically shaped wall 19 of the exemplary HAT apparatus is approximately 0.125 meters thick.

The cylindrical wall 19 of the chamber 11 of the exemplary HAT apparatus 10 is made of a steel reinforced concrete tube, normally used for underground water piping. The bottom wall 18 of the chamber 11 is made of steel. Of course, it is not a requirement that the chamber 11 be constructed of a concrete material, or that the bottom wall 18 be constructed of steel. The chamber 11 could also be constructed of a variety of other materials, for example, high density PVC, fiberglass, or similar materials. Indeed, it is not even a requirement that the chamber walls 18, 19 be acoustically rigid, though structural rigidity is preferred. However, the acoustic rigidity of the walls 18, 19 of the chamber 11 causes a high degree of acoustic reflection. If the walls 18, 19 are not acoustically rigid, the acoustic field energy is less uniform and more frequency dependent due to flexing of the walls. Although the acoustic performance of such a device might be somewhat poorer, the advantages of lighter weight and lower cost might make such a design more desirable and such a design is encompassed within the scope of the present invention.

The chamber 11 has an orifice 22 along a bottom wall 18. The orifice 22 is located at approximately the center of the bottom wall 18 and is covered by a flexible membrane 23. This membrane 23 may be manufactured of any appropriate flexible material, such as latex rubber. The membrane 23 is securely attached to the bottom wall 18 at the sides of the orifice 22 with an adhesive—such as Neoprene Gel, for example.

A piston 24 is positioned directly under and in contact with the membrane 23. The piston 24 comprises a piston head 26 and a shaker arm 27. The shaker arm 27 connects the piston head 26 to a shaker apparatus 28, such as a Vibration Test Systems VTS 100 permanent magnet shaker. The piston 24 basically forms an acoustic generator that causes the membrane 23 to oscillate and generate acoustic waves in the fluid 12. While this particular shaker 28 is not required, the VTS 100 shaker has a maximum rated force peak sine wave of 100 lbf. or 444 N. This force output is adequate to generate the preferred amplitude of acoustic force, as will be discussed below. One with ordinary skill in the art could easily select a different shaker apparatus of the appropriate size, if desired.

The shaker apparatus 28 is mounted on a support frame 29 underneath the chamber 11 and attached via a power cord 31 to an amplifier 32. An amplifier 32 to match the particular preferred shaker 28 is included in the VTS 100 package and is a solid state Crown Int. CE2000 amplifier with selectable voltage/current modes (model VTS 1991). In certain configurations of a shaker 28, a separate amplifier 32 may not be necessary. The amplifier 32, and in turn the shaker 28, is preferably driven by a computer 33. The exemplary HAT apparatus 10 uses LABVIEW™ software on the computer 33 to control the amplitudes and frequencies of the shaker 28 and the piston 24. Other types of software could be used to control the shaker 28 and piston 24, for example, custom-designed software. The computer 33 has the capability to convert analog input signals to digital and to convert digital signals to analog output. This is preferably accomplished with an Analog to Digital card in the computer 33.

While the piston 24/shaker 28 arrangement described above is a preferred acoustic generator, or the preferred method for generating acoustic waves in the fluid 12, other arrangements are possible. Indeed, it is possible to generate acoustic waves in the fluid 12 of proper frequencies and amplitudes using one or more commercially available underwater loudspeakers or transducers (either commercially available or custom designed) placed directly in the water. For example, electrodynamic, piezoelectric, hydraulic, magnetic, and electrostatic transducers could all be used with a HAT apparatus 10. One such other embodiment is described below in reference to FIG. 2. One having ordinary skill in the art would appreciate other ways of generating acoustic waves in the fluid 12 and these are all intended to be included within the scope of the present disclosure.

The size and materials of the piston head 26 are not critical to the present invention provided that the combination of piston 24, shaker 28, and amplifier 32 are capable of producing the required acoustic sound pressure levels at the lungs at the appropriate frequencies. However, the preferred piston head 26 is constructed of aluminum and is 0.29 meters in diameter with a 0.01 meter thickness. Certainly other sizes, shapes, and construction materials may be just as effective with the HAT apparatus 10. One having ordinary skill in the art would be well aware of such variations and these variations are intended to be included in the scope of the present disclosure.

As noted above, in the exemplary HAT apparatus 10, the chamber 11 is filled with a fluid 12. In the preferred embodiment, this fluid 12 comprises water. Water has been selected as the preferred fluid 12 because so much of the human body is composed primarily of water. Indeed, only the human bones and the lungs are not primarily made of water. Because the human body is mostly water, there is no acoustical impedance mismatch across the transition from water to human flesh, blood, visceral organs, etc. . . . However, under certain circumstances as would be understood with one having ordinary skill in the art, another fluid 12 may be used in the HAT apparatus 10.

The chamber 11 has a drain opening 34 and a fill opening 36 in the bottom wall 18 of the chamber 11. The drain and fill openings 34, 36 can be of any appropriate size and are for draining the fluid 12 out of the chamber 11 and then replacing new fluid 12 into the chamber 11 respectively. The drain and fill openings 34, 36 may be equipped with appropriate covers 37, 38. Alternatively, one opening could be used to drain and fill the chamber 11. Also, one could elect to fill and drain the chamber 11 from the top 21 of the chamber, such as with a pump.

The chamber 11 also has a pair of fluid circulation openings 39a, 39b in the chamber sidewall 19. Preferably, a fluid pump 41 is in communication with the circulation openings 39a, 39b by an outflow pipe 42 attached to the first opening 39a and an inflow pipe 43 attached to the second opening 39b. This permits the fluid 12 to be pumped out of the chamber 11, through the pump 41, and back into the chamber 11. This external circuit 41, 42, 43 keeps the fluid 12 circulating in the chamber 11. In the preferred embodiment 10, the pump 41 is in the form of a hot tub/spa water pump, such as an 87 liters per minute Gundfos water pump, for example.

Also, it is preferred that the fluid 12 be heated to approximately 35° C., near body temperature, in order that a person 13 in the chamber 11 will be comfortable while in the fluid 12. For this reason, a water heater 44 is preferably connected along the inflow pipe 43. It is possible to raise the temperature of the fluid 12 to a level higher than body temperature. This increased temperature may result in decreasing the viscosity of the sputum in the patient and possibly increasing the effectiveness of HAT. In the preferred embodiment, the water heater 44 is in the form of a hot tub/spa water heater, such as a Vulcan Electric Company 6 kilowatt heater.

Within the chamber 11 of the preferred HAT apparatus 10, there is positioned a supporting structure 17 such that a person 3 undergoing treatment can sit in the fluid 12. The supporting structure 17 should preferably be positioned such that the patient's head 14 protrudes from above the fluid surface 16, as shown in FIG. 1. Because patients come in different sizes, the supporting structure 17 is preferably adjustable.

Although any seat, or other similar structure may be used in the preferred embodiment 10, the preferred supporting structure 17 comprises an inflatable chair 46 supported by an adjustable frame 47 constructed of PVC pipe. The inflatable chair 46 is filled with the fluid 12, and not air. In this way, any acoustical waves traveling through the chamber fluid 12 will not "see" or be influenced by the chair 46 and will be transmitted through the chair 46 just as through the other fluid 12 in the chamber 11. Similarly, PVC has a very similar impedance to water, and if the fluid 12 is water, the frame 47 will also not substantially affect the transmission of acoustic waves through the fluid medium 12 in the chamber 11.

In the preferred embodiment of a HAT apparatus 10, the chamber 11 is supported off of the ground 48 and above the piston 24/shaker 28 assembly by a structure 49. The structure 49 also supports a working platform 51. Of course, the platform 51 and the particular structure 49 depicted in FIG. 1 are not required. The structure 49 is comprised of steel support and the platform 51 is preferably comprised of wood.

Because the objective of the present device 10 is such that a person 13 can be placed in the chamber 11, it is preferred that a ladder 52 be supplied in order to permit easy ingress and egress from the chamber 11. Obviously, steps could be constructed to also permit easy ingress and egress from the chamber 11. Additionally, depending on the size of the chamber 11, it may be desirable to use another ladder (not shown) on the inside of the chamber 11 to permit a patient to descend into the chamber 11.

As depicted in FIG. 1, a patient 13 is preferably seated in the chair 46. The frame 47 is then adjusted such that the top surface 16 of the fluid 12 is at about a neck 53 of the patient 13. Then, a hydrophone 54 is preferably affixed about a chest region 56 of the patient 13.

Basically, a hydrophone is a device that responds to the pressure associated with underwater sound waves and converts this response into electrical energy at a certain voltage amplitude proportional to the pressure amplitude of the sound waves. The voltage generated by a hydrophone can be read on a meter or by a computer through an analog to digital converter. A hydrophone can be thought of as the underwater equivalent of the microphone. A hydrophone such as a Bruel & Kjaer 8103 piezoelectric hydrophone is preferred. The hydrophone 54 in FIG. 1 is connected to the computer 33 by a data cable 57.

The hydrophone 54 is positioned adjacent to the chest 56 of the patient 13, just below the sternum. Then, an adjustable Velcro™ strap 58 is positioned around the patient's chest 56 and secures the hydrophone 54 to the chest 56 of the patient 13. Preferably, the strap 58 is somewhat flexible and will expand with the breathing of the patient 13. The strap 58 is positioned so that it overlies the cable 57 that connects the hydrophone 54 to the computer 33, as depicted in FIG. 1. The goal of using the Velcro strap 58 is to prevent, or minimize, the hydrophone 54 from moving relative to the patient 13. As such, other common and well-understood devices and methods to attach the hydrophone 54 to the patient 13 may be used. For example, an adhesive such as tape, glue, or the like could secure the hydrophone 54 to the patient's chest 56.

The hydrophone 54 monitors the level of acoustic excitation imparted on the patient 13 during treatment, as described in detail below. This monitoring assists in maintaining a safe and effective treatment environment. The hydrophone 54 relays to the computer 33 signals from which can be determined the frequency and amplitude at which a person's lungs are oscillated.

The exemplary HAT apparatus 10 described above and pictured in FIG. 1 is only an example of a HAT apparatus. An alternative embodiment of a HAT apparatus would be a HAT apparatus more suited for home use. For example, the chamber could comprise a bath tub, jacuzzi, or whirlpool/spa. A simple underwater speaker or transducer system could be used to deliver the acoustic waves into the water chamber. Such alternative apparatuses are intended to be encompassed within the scope of the present invention.

Figure 2:
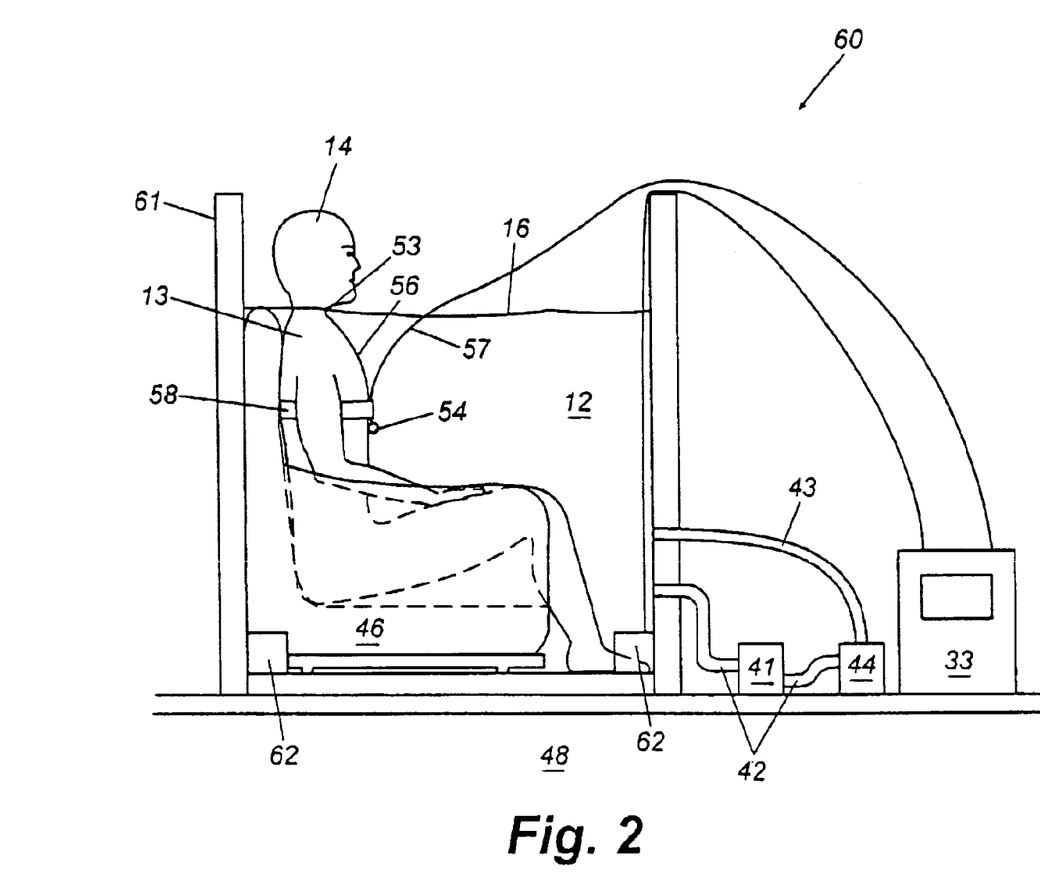
FIG. 2 is a cut-away side view of a second exemplary embodiment of a device for hydro-acoustic therapy for the lungs.

FIG. 2 depicts an alternative embodiment of a HAT apparatus 60 particularly suited for home use. The alternative HAT apparatus 60 is very similar to the first exemplary HAT apparatus 10, however, the chamber 61 is preferably constructed of a plastic or fiberglass material. Additionally, the chamber 61 is smaller than the chamber 11 of the first exemplary HAT apparatus depicted in FIG. 1. For example, where the chamber 11 of FIG. 1 is approximately 5 feet tall and 4 feet in diameter, the chamber 61 of the alternative embodiment 60 may be approximately 3 feet tall and only 3 feet in diameter.

Additionally, in the alternative embodiment of a HAT apparatus 60 a piston is preferably not used as an acoustic generator, but a transducer device, or series of transducer devices 62, are used. The preferred home HAT apparatus 60 uses an array of underwater speakers 62 as acoustic generators.

With the exception of the material used for the chamber 61, the size of the chamber 61 (which can be smaller than the chamber 11 described above), and the use of underwater speakers 62 to generate acoustic waves, the other primary elements of the preferred home HAT apparatus 60 are the same as the HAT apparatus 10 of FIG. 1. Indeed, the home HAT apparatus 60 also has a computer 33 to drive the speaker array 62 at a selected amplitude and frequency. The chamber 61 of the HAT apparatus 60 also has circulation openings 39a, 39b in fluid communication with a pump 41 and a heater 44.

The HAT apparatus 60 also preferably has a supporting structure 17 comprising a chair 46 and an adjustable frame in the chamber 61. A hydrophone 54 is also affixed to the chest 56 of the patient 13 and connected to the computer 33 via a data cable 57. The hydrophone 54, as above, permits the computer 33 to monitor and control the treatment process. Notice that with the home embodiment 60, the chamber 61 is preferably designed with no supporting structure 49.

II. Operation of the Preferred Embodiment

The operation of the HAT apparatus 10 depicted in FIG. 1 will now be described in a preferred method of implementing HAT treatment for a patient 13. It should be understood that the method described below is also equally applicable to the alternative embodiment 60 depicted in FIG. 2 and other possible embodiments of a HAT apparatus.

In the preferred method for HAT treatment, the HAT apparatus ensonifies a patient 13 with acoustic waves at specified frequencies. The patient's lungs are thereby caused to vibrate and respiratory secretions are mobilized in order to be removed from the lungs by the patient 13.

The present invention is not limited to operation at a particular frequency, although low frequencies are generally desirable in HAT. For example, the frequencies used are generally below 120 Hertz. Although there is no required frequency of operation, operation at a fundamental resonant frequency of a patient's lung is desired. Operation at the resonant frequency is desirable from an efficiency standpoint in that the patient's lungs would exhibit the maximum response for the least amount of energy input. Additionally, when the lung is excited at its resonant frequency, the result is that the lung responds in its fundamental oscillatory mode. That is, all the lung tissue moves uniformly, leading to more effective therapy.

The amount of energy put into the acoustic waves (the amplitude of the waves) is of some importance in that the amplitude of the acoustic waves should preferably be kept below a level that might cause physical harm to a patient 13. While the actual amplitude limit depends on a variety of factors, it is preferred, and well-within safety limits, to keep the sound pressure level used in HAT to below 160 dB re 1 $\mu$Pa, as measured in the fluid 12 at the lungs. This level corresponds to safety levels established by the United States Navy. However, the safety limit of 160 dB re 1 $\mu$Pa is based in large part on the more restrictive sensitivity of a person's head to acoustic vibrations. Since the head 14 of the patient 13 is above the fluid 12, the exemplary HAT apparatus 10 and could very well operate safely at amplitudes above 160 dB re 1 $\mu$Pa.

It is preferred that the pressure amplitude is high enough to be of therapeutic value. It has been determined in clinical tests that a level of at least 158 dB re 1 $\mu$Pa is therapeutic. Of course, the present invention is expressly not limited to a specific pressure amplitude and may be operated at a lower (or higher) amplitude level. Indeed, lower pressure amplitudes may be preferred if proven to be therapeutic. The computer 33 is programmed to maintain the pressure level at the lung (as measured by the hydrophone 54) at a therapeutic and safe level, 158 dB re 1 $\mu$Pa in the preferred embodiment.

Because the resonant frequency of each individual's lung is different, and the resonant frequency of a given individual's lung may vary from day to day, the first step of the preferred treatment is to determine the resonant frequency of the patient's lungs. This step is not absolutely necessary, however, because as noted above, the particular frequency of operation is not critical to the present invention.

A. Determination of the Resonant Frequency

Figure 3:
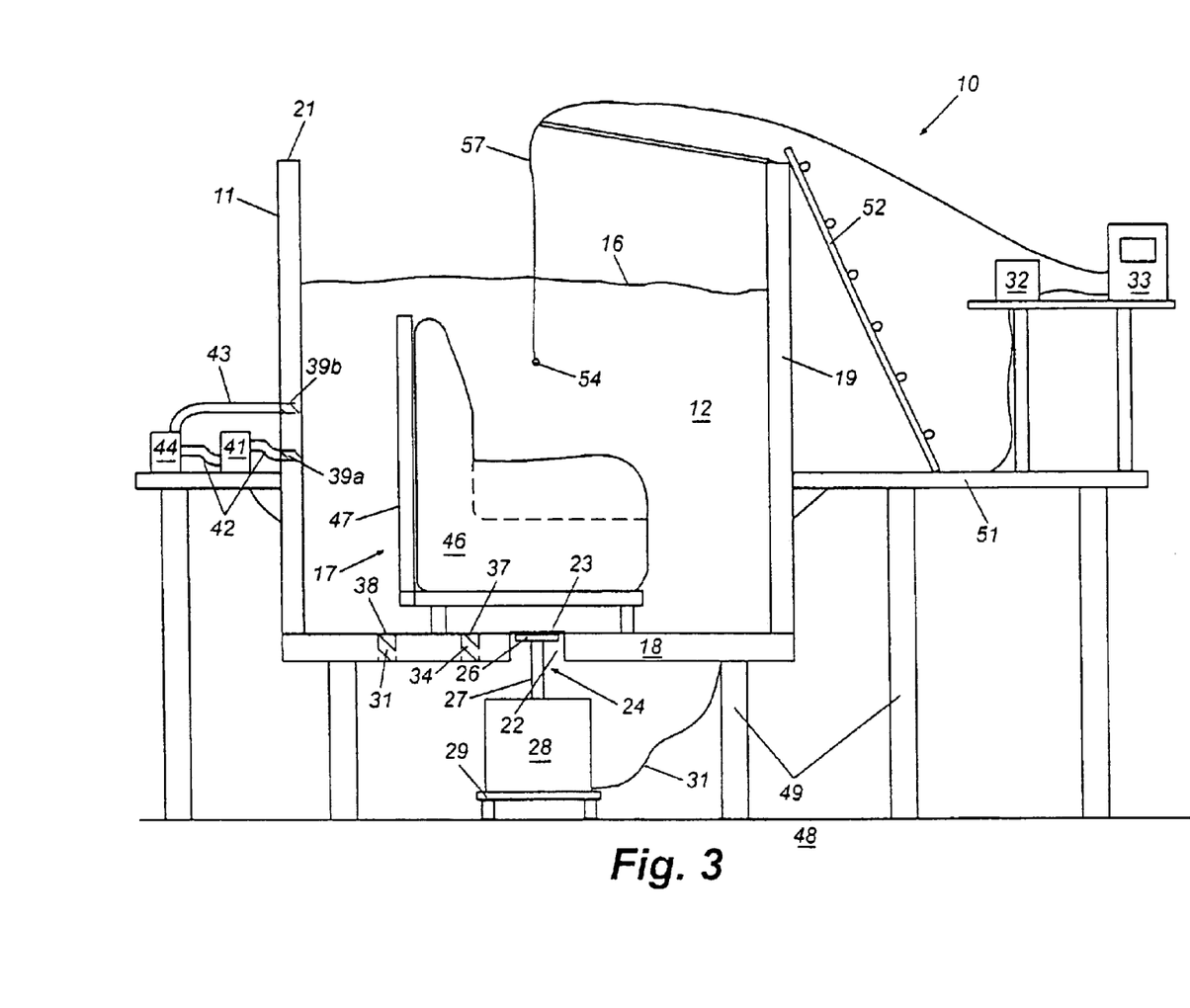
FIG. 3 is a cut-away side view of the exemplary hydro-acoustic therapy device of FIG. 1 without a patient.

As depicted in FIG. 3, a first step in determining a resonant frequency of a patient's lungs is to begin with a chamber 11, as described above in reference to FIG. 1 without a patient 13 in the chamber 11. FIG. 3 depicts such an "empty" chamber 11. Then the hydrophone 54 that will be used on the patient 13, as described above in reference to FIG. 1, is lowered into the fluid 12 in the chamber 11. The level of the fluid 12 is adjusted such that it is the same height on the side wall 19 of the chamber 11 as when the patient 13 was seated in the chair 46.

Once the hydrophone 54 is lowered into the fluid 12, the shaker 28 is activated, which drives the piston 24 resulting in the membrane 23 flexing into and out of the chamber interior. The activation of the shaker 28/piston 24/membrane 23 creates acoustic waves in the fluid 12. The hydrophone 54 is used to monitor the acoustic waves.

The piston 24 begins moving at 24 Hertz and the frequency of movement is increased at the rate of approximately 1 Hertz per second to a maximum of 120 Hertz. Of course, this is just one example of how the frequency may be varied with time. For example, the frequency could begin at 120 Hertz and move downward to 24 Hertz, or another value, at different steps. The driving voltage is preferably kept constant at a level that maintains the amplitude of the acoustic waves, as measured at the hydrophone 54, several dB below the preferred therapeutic value of about 158 dB re 1 $\mu$Pa.

The hydrophone 54 measures the response in the fluid 12 to the acoustic waves generated by the oscillation of the membrane 23. This is converted to electrical signals and relayed to the computer 33. This first set of hydrophone data is band pass filtered, amplified, and digitized to be recorded by the computer for analysis. Once this first set of digitized hydrophone data is collected by the computer 33, the piston 24 ceases operation. Note that this measurement needs to be done only once since typically nothing changes with the device. This task comprises a calibration of the internal acoustic field.

The next step in the preferred method for determining the resonant frequency of a patient's lungs is to remove the monitor hydrophone 54 and permit a patient 13 to enter the chamber 11 and be seated on the chair 46. Then, as described in reference to FIG. 1 above, the hydrophone 54 is affixed to the chest 56 of the patient 13. FIG. 1 depicts the appropriate configuration for this next step.

Once the hydrophone 54 is affixed adjacent to the patient's chest 56, the shaker 28 is activated which drives the piston 24 resulting in the membrane 23 flexing into and out of the chamber interior, which creates acoustic waves in the fluid 12. The piston 24 begins moving at 24 Hertz and the frequency of movement is increased at the rate of approximately 1 Hertz per second to a maximum of 120 Hertz. During the determination of the resonance frequency, the driving voltage is kept constant at a level that maintains the amplitude of the acoustic waves as measured at the hydrophone 54 several dB below the therapeutic value. As noted above, the preferred therapeutic value is about 158 dB re 1 $\mu$Pa, as measured in the fluid 12 at the patient's lungs.

During the time that the patient's body 13 is ensonified by the acoustic waves, the hydrophone 54 measures the response of the patent's lungs. This is converted to electrical signals and relayed to the computer 33. The hydrophone data is band pass filtered, amplified, and digitized to be recorded by the computer for analysis. This data forms a second set of hydrophone data, as the first set of hydrophone data was collected as described above in reference to FIG. 3, while no patient 13 was in the fluid 12.

The acoustic waves are generated by the membrane 23 and travel through the fluid 12, which is water in this embodiment, to the patient's body 13. At the patient's body 13, the waves remain largely unchanged as the body 13 is mostly water. The waves then travel through the patient's body 13 until the waves reach the boundary of the lungs. Because the lungs are largely air, there is an impedance and compliance mismatch at the lung surface and the lungs are caused to vibrate at the frequency of the acoustic wave. As noted above, at resonance, the lungs respond in a fundamental oscillatory mode with a relatively large amplitude. This results in uniform movement of the lung tissue, and not just movement of the air in the lungs.

The hydrophone 54 measures the vibration of the lungs by detecting and measuring the acoustic pressure within the lungs generated by the underwater sound waves. Once the digitized hydrophone data is collected by the computer 33, the piston 24 ceases operation.

Alternatively, the resonant frequency of the lungs could be determined by affixing one or more accelerometers to the chest 56 of a patient 13 and then going through the same process of ensonifying the patient 13 with acoustic waves of varying frequency. The accelerometers would measure the response of the patient's lungs by showing the acceleration and hence the displacement of the patient's chest 56. The disadvantage to this second preferred method is that the accelerometers must be securely affixed to the chest of the patient. Using a hydrophone is less intrusive to the patient.

Alternatively, an ultrasound vibrometer could be used to determine resonant frequency of a patient's lungs. However, this method generally involves more costly equipment that is not necessary in the present treatment process.

To summarize, the computer 33 gathers two sets of digitized hydrophone data: a first set without a patient 13 in the fluid 12 (see FIG. 3) and a second set of data with the patient 13 seated in the fluid 12 (see FIG. 1). Then, the computer 33 is caused to normalize the two sets of hydrophone data (one set with patient 13 and one set without patient 13) and plot the collected data, such as with a computer program like LABVIEW, Matlab or other similar software. The resonant frequency of the patient's lungs can be determined from the plot.

To normalize and plot the data, the computer 33 first computes a transfer function for the first set of data (with the patient 13 in the chamber 11) as a function of the frequency of the piston 24. The computer 33 also computes a transfer function for the second set of data (without the patient 13 in the chamber 11) as a function of the frequency of the piston 24. This procedure is well understood by those having ordinary skill in the art.

The computer 33 then takes the ratio of the two transfer functions to arrive at a new normalized amplitude transfer function that will be used for determining the resonant frequency of the patient's lungs. In other words the computer 33 makes the following computation:

$$Y = (ampl_{lung})/(ampl_{input})$$

Where:

Y is a transfer function of the normalized amplitude as a function of frequency;

$ampl_{lung}$ is a transfer function of the amplitude of the lung's response with the patient 13 in the chamber 11 (the second set of data); and $ampl_{input}$ is transfer function of the amplitude of the acoustic pressure in the chamber 11 in the absence of the patient 13 (the first set of data).

In other words, the computer 33 arrives at a normalized amplitude by computing the ratio of the amplitude of the lungs' vibratory response to the acoustic waves to the input acoustic pressure. The input acoustic pressure is the amplitude of the acoustic pressure in the chamber 11 under identical drive conditions, measured by the same hydrophone 54 in approximately the same location with the patient 13 not in the chamber 11. This latter measurement is made with the level of fluid 12 in the chamber 11 set to be the same as it is when the patient 13 is in the chamber 11. By using the driving the piston 24 as described above, one obtains the transfer function Y as a function of excitation frequency. This transfer function Y is then plotted by the computer 33 versus the frequency of excitation of the piston 24.

Figure 4:
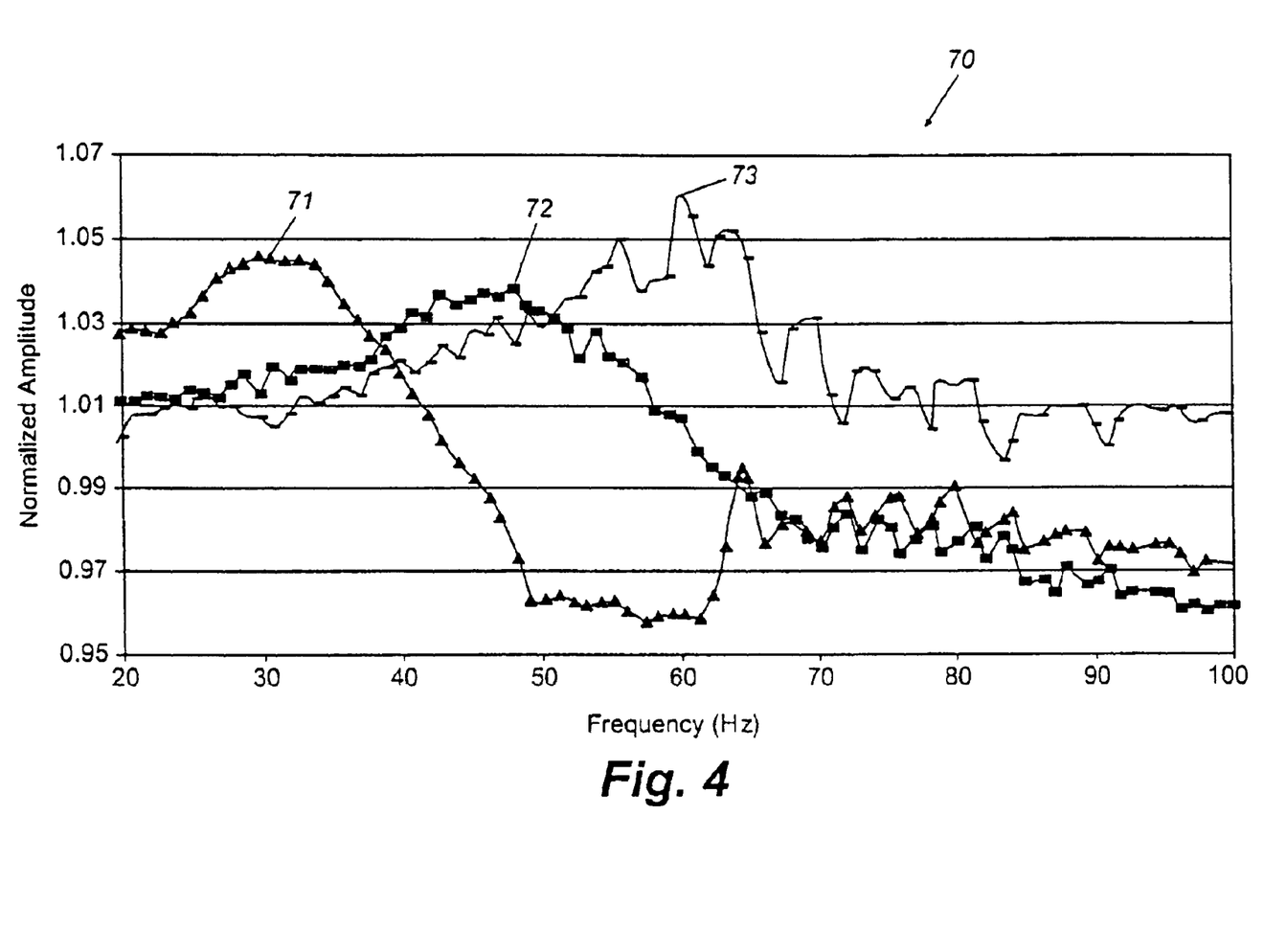
FIG. 4 is an exemplary plot of normalized amplitude versus frequency for determining a resonant frequency of a patient's lungs.

FIG. 4 is a plot 70 for three typical patient's lungs responding to the acoustic waves during the resonant frequency test described above. FIG. 4 is a plot 70 of the normalized amplitude of the lung's vibratory response versus the frequency of the piston 24, in Hertz. The normalized amplitude is plotted along the y-axis and the frequency is plotted along the x-axis. Note that the oscillations in the curves are due to the breathing of the patient 13.

The resonant frequency of the patient's lungs is identified in the plot by the frequency corresponding to the maximum normalized amplitude on the curve associated with the patient. The three curves in the example plot 70 have a maximum of approximately 31 Hertz for patient 1 (71), 49 Hertz for patient 2 (72), and 60 Hertz for patient 3 (73). These are typical resonant frequencies for patients.

It should be noted that the underwater resonance frequency of the lungs is orders of magnitude lower than for any other organ of the body. Resonance of a patient's lungs is a "spring-mass" resonance, where the compliance of the air filled lungs is the spring and the radiation mass of the surrounding fluid is the mass. The frequency is low because the lungs comprise a very soft spring which resonates against the very large radiation mass of the fluid. This is not a half wave-length type resonance. This resonance of the lungs, as described above, does not exist in air.

The maximum point 71, 72, 73 and the corresponding resonant frequency can be identified by the computer 33 automatically, by an operating technician or by the patient him/herself. If the computer 33 identifies the resonant frequency automatically, it is not necessary for the computer to actually printout a plot 70 of the data. A computer 33 can be programmed so as to identify the maximum point in a series of data without having a need to physically plot the data.

B. Treatment Procedure

For the preferred HAT treatment method, the patient 13 is seated within the chamber 11, as depicted in FIG. 1. The patient 13 is seated such that the level of the fluid 12 is approximately at the base of the patient's neck 53. In this way, the entire surface of the patient's lungs is surrounded by the chamber fluid 12. Having the patient's lungs surrounded by the chamber fluid 12, is preferable because the fully submerged lungs receive acoustic pressure stimulation throughout the whole mass. Indeed, a limitation of the previous VEST™ therapy is that the lungs are not uniformly stimulated.

Once the patient 13 is comfortable in the chamber 11, the therapy begins. The therapy involves causing the piston 24 to oscillate at a certain frequency or group of frequencies. The piston 24 causes the membrane 23 to oscillate a certain frequencies and amplitude, which, in turn, generates acoustic waves in the fluid 12. The acoustic waves transmit through the fluid 12 to the surface of the patient's body 13.

The vast majority of the organs of the human body are primarily composed of water. Only the lungs and the bones of a patient 13 are not primarily composed of water. Since the fluid 12 in the chamber 11 is water, the human body, with the exception of the lungs and the bones, is acoustically transparent in the water 12. In other words, the water 12 in the chamber 11 and the body's organs are matched in impedance and compliance. Because of the match, most visceral organs do not exhibit significant responses to an applied underwater acoustic field.

In contrast, the air-water interface at the lung pleural surface provides an acoustic impedance and compliance mismatch. Due to the mismatch at the lung pleural surface, when the lung is exposed to an acoustic field, the lung is excited and begins to vibrate. As depicted in FIG. 4, the amplitude at which the lung vibrates changes as the frequency of the acoustic waves change.

As noted above, it is desirable for the treatment to occur at the resonant frequency of the lung and at a pressure amplitude of approximately 158 dB re 1 $\mu$Pa. This ensures the most efficient transmission of energy from the acoustic waves to the lung surface. Furthermore, when the lung is submersed in water, and is stimulated at its resonance frequency underwater (which is usually different than the resonant frequency of a lung when not submersed in water), the lung surface oscillates uniformly at a fundamental oscillatory mode. The lung itself actually moves in uniform motion. This response is in contrast to a response of a patient's lung excited at its resonant frequency when the patient is not submersed in water. A patient that is not submersed exhibits a resonant response that results primarily in the movement of the air within the lung (Helmholtz Resonance).

In an exemplary procedure using the HAT apparatus 10 the treatment will take only thirty minutes. For ten minutes, the HAT apparatus 10 will generate acoustic waves at a frequency below the resonant frequency of the lung. In the exemplary implementation, the first frequency will be approximately 10 Hertz below the resonant frequency of the patient's lungs. The amplitude of this excitation is preferably 158 dB re 1 $\mu$Pa as measured by the monitoring hydrophone. Then, for ten minutes the piston 24 will operate at the resonant frequency of the patient's lungs. Although not required, the driving voltage amplitude may be lowered during this phase of the treatment to maintain the pressure amplitude at the lung at the same level 158 dB re 1 µPa. Finally, the piston 24 will operate at 10 Hertz greater than the resonant frequency of the person's lungs again at voltage level chosen to produce a pressure of 158 dB re 1 µPa at the lungs.

For example, in a typical patient, the piston 24 would operate at 30 Hz so as to generate an applied pressure amplitude of 158 dB re 1 µPa for ten minutes, at 40 Hz so as to generate an applied pressure amplitude of 158 dB re 1 µPa for ten minutes, and finally at 50 Hz so as to generate an applied pressure amplitude of 158 dB re 1 µPa for ten minutes. Of course, this is just an example of a somewhat typical treatment which has been found to be effective and safe. Treatment times and frequencies, waveforms and amplitudes may be varied, for example broadband or multiple frequency signals within the frequency range may be utilized. For example, the frequency and amplitude of the acoustic waves may be varied as a function of time. On the other hand, it may be desirable in certain HAT treatment scenarios to cause the acoustic waves to be pulsed through the liquid.

After receiving the HAT treatment, the patient 13 is removed from the chamber 11. The patient 13 may then engage in a period of huffing and coughing to remove sputum from the patient's lungs. Hufffing and coughing to remove sputum from the patient's lungs may also be performed while patient is still in the water undergoing HAT therapy.

The HAT apparatus and treatment method described above will be beneficial for the treatment of patients having cystic fibrosis. Additionally, the HAT apparatus and treatment method may be used with any condition that would benefit from a lung therapy that assists in the mobilization of respiratory secretions. For example, the HAT apparatus and treatment method may be useful in treatments of chronic obstructive lung disease, pneumonia, and lung cancer.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

We claim:

1. A method for determining a resonant frequency of lungs of a patient, comprising the steps of:
    providing a chamber containing a fluid;
    placing a hydrophone in said chamber;
    causing acoustic vibrations at a first frequency and changing a frequency of said acoustic vibrations to a second frequency;
    recording a first output of said hydrophone as said acoustic vibration frequency is increased;
    computing a first transfer function of said first output;
    placing a person in said chamber such that a body of the person is immersed in said fluid;
    positioning said hydrophone near a chest area of the person;
    causing acoustic vibrations at said first frequency and changing said frequency of said acoustic vibrations to said second frequency;
    recording a second output of said hydrophone as said acoustic vibration frequency is increased;
    computing a second transfer function of said second output;
    plotting a ratio of said first transfer function to said second transfer function versus said frequency of said acoustic vibrations; and
    identifying a maximum of said plot as a resonant frequency of said lung.

2. An apparatus for administering hydro-acoustic therapy for a patient, said device comprising:
    a chamber having a volume of water, said chamber further comprising rigid walls defining a generally cylindrical chamber, wherein said chamber further comprises an orifice in a wall, said orifice covered by a flexible membrane;
    a supporting structure in said chamber for permitting a person to sit in said chamber, partially submersed in said water, during treatment;
    a hydrophone positioned near a chest of said person in said water, said hydrophone for monitoring a response of said person to said acoustic waves; and
    a piston outside of said chamber directed to press against said membrane in order to cause said membrane to oscillate in periodic motion, said piston thereby generating acoustic waves in said water of said chamber, wherein said acoustic waves are low frequency vibrations.

3. A method for determining a resonant frequency of lungs of a patient, comprising the steps of:
    providing a chamber containing a fluid;
    placing a hydrophone in said chamber;
    causing acoustic vibrations in said fluid at a first frequency and changing a frequency of said acoustic vibrations to a second frequency;
    processing a first output of said hydrophone as said acoustic vibration frequency is changed;
    placing a person in said chamber;
    positioning said hydrophone near the person;
    causing acoustic vibrations in said fluid at a third frequency and changing said frequency of said acoustic vibrations to a fourth frequency;
    processing a second output of said hydrophone as said acoustic vibration frequency is changed; and
    comparing said first processed output to said second processed output such as to identify a resonant frequency of said lung.

4. The method of claim 3, wherein said processing of said first and second output comprises normalizing said first and second outputs.

5. The method of claim 4, wherein said normalizing comprises:
    computing a first transfer function of said first output; and
    computing a second transfer function of said second output.

6. The method of claim 5, wherein said comparing step comprises:
    plotting a ratio of said first transfer function to said second transfer function versus said frequency of said acoustic vibrations; and
    identifying a maximum of said plot as said resonant frequency of said lung.

7. The method of claim 4, wherein said processing step further comprises filtering, amplifying, and digitizing said first and second outputs.

8. The method of claim 3, wherein said positioning step comprises placing said hydrophone in substantially the same position within said chamber as the hydrophone was placed when the person was not in the chamber.

9. A method for the medical treatment of a person, said method comprising:
providing a chamber containing a fluid;
placing a person in said chamber such that a body of the person is immersed in said fluid;
determining a resonance frequency of a lung of said person;
introducing acoustic vibrations into said fluid, said acoustic vibrations having a frequency; and
sequentially adjusting the frequency of said acoustic vibrations between a first frequency and a second frequency, wherein one of said frequencies comprises said resonance frequency and the other of said frequencies comprises a frequency either greater than or less than said resonance frequency.

10. The method of claim 9, wherein said first frequency comprises said resonance frequency and said second frequency comprises a frequency less than said resonance frequency.

11. The method of claim 10, wherein said acoustic vibrations comprise an amplitude of about 158 dB re 1 $\mu$Pa.

12. The method of claim 11, wherein said sequential adjusting step comprises setting the frequency of said acoustic vibrations to a first frequency for about ten minutes and then setting the frequency of said acoustic vibrations to a second frequency for about 10 minutes.

13. The method of claim 9, wherein said first frequency comprises a frequency less than said resonance frequency and said second frequency comprises said resonance frequency.

14. The method of claim 13, wherein said acoustic vibrations comprise an amplitude of about 158 dB re 1 $\mu$Pa.

15. The method of claim 14, wherein said sequential adjusting step comprises setting the frequency of said acoustic vibrations to a first frequency for about ten minutes and then setting the frequency of said acoustic vibrations to a second frequency for about 10 minutes.

16. The method of claim 9, wherein said first frequency comprises said resonance frequency and said second frequency comprises a frequency greater than said resonance frequency.

17. The method of claim 16, wherein said acoustic vibrations comprise an amplitude of about 158 dB re 1 $\mu$Pa.

18. The method of claim 17, wherein said sequential adjusting step comprises setting the frequency of said acoustic vibrations to a first frequency for about ten minutes and then setting the frequency of said acoustic vibrations to a second frequency for about 10 minutes.

19. The method of claim 9, wherein said first frequency comprises a frequency greater than said resonance frequency and said second frequency comprises said resonance frequency.

20. The method of claim 19, wherein said acoustic vibrations comprise an amplitude of about 158 dB re 1 $\mu$Pa.

21. The method of claim 20, wherein said sequential adjusting step comprises setting the frequency of said acoustic vibrations to a first frequency for about ten minutes and then setting the frequency of said acoustic vibrations to a second frequency for about 10 minutes.

22. The method of claim 21, wherein said placing step comprises immersing the person in said fluid such that a body of the person is fully immersed in said fluid below a neck area of the person.

23. The method of claim 22, wherein said fluid comprises water.

24. The method of claim 23, further comprising the step of positioning a monitoring device near a chest area of the person such that an effect of said acoustic vibrations on the person is monitored.

25. The method of claim 24, wherein said monitoring device comprises a hydrophone.

* * * * *